(12) United States Patent
Roth

(10) Patent No.: US 9,681,978 B1
(45) Date of Patent: Jun. 20, 2017

(54) MOUTH GUARD FOR THE PREVENTION OF JAW CLENCHING AND TEETH GRINDING

(71) Applicant: Karen Q. Roth, Hillsdale, NJ (US)

(72) Inventor: Karen Q. Roth, Hillsdale, NJ (US)

( * ) Notice: Subject to any disclaimer, the term of this patent is extended or adjusted under 35 U.S.C. 154(b) by 239 days.

(21) Appl. No.: 14/627,146

(22) Filed: Feb. 20, 2015

Related U.S. Application Data

(60) Provisional application No. 61/966,381, filed on Feb. 24, 2014.

(51) Int. Cl.
*A61C 5/14* (2006.01)
*A61F 5/56* (2006.01)

(52) U.S. Cl.
CPC .......... *A61F 5/56* (2013.01); *A61F 2005/563* (2013.01)

(58) Field of Classification Search
CPC ....... A61F 5/56; A61F 2005/563; A61F 5/566
USPC .................................................. 128/861, 848
See application file for complete search history.

(56) References Cited

U.S. PATENT DOCUMENTS

| | | | | |
|---|---|---|---|---|
| 5,732,715 A * | 3/1998 | Jacobs | ................ | A63B 71/085 128/861 |
| 5,795,150 A * | 8/1998 | Boyd | ...................... | A61F 5/566 128/861 |
| 5,915,385 A * | 6/1999 | Hakimi | ................... | A61F 5/566 128/848 |
| 5,941,246 A * | 8/1999 | Roopchand | ....... | A61M 16/0488 128/207.14 |
| 6,895,970 B1 * | 5/2005 | Lawrence | ............... | A61F 5/566 128/848 |
| 2004/0038172 A1 | 2/2004 | Jacobs | | |
| 2007/0028926 A1 * | 2/2007 | Kotani | ..................... | A61F 5/566 128/848 |
| 2008/0099029 A1 * | 5/2008 | Lamberg | ................. | A61F 5/566 128/848 |
| 2008/0199824 A1 * | 8/2008 | Hargadon | ............... | A61F 5/566 433/6 |
| 2011/0005526 A1 * | 1/2011 | Garabadian | ............. | A61F 5/566 128/848 |
| 2011/0162658 A1 * | 7/2011 | Fisher | ..................... | A61F 5/566 128/848 |
| 2011/0308532 A1 * | 12/2011 | Nelissen | ................. | A61F 5/566 128/848 |
| 2012/0255563 A1 * | 10/2012 | Thornton | ................. | A61C 7/08 128/861 |
| 2013/0130193 A1 | 5/2013 | Fisher et al. | | |
| 2014/0190491 A1 * | 7/2014 | Garcia | ..................... | A61C 5/14 128/861 |

\* cited by examiner

*Primary Examiner* — Kristen Matter

(57) ABSTRACT

The invention provides mouth guards sized and configured to prevent jaw clenching and teeth grinding and methods of using the mouth guards. One embodiment provides a one-piece mouth guard made of a semi-rigid, springy, flexible polymer that includes an arcuate tray portion having a front, a rear, a top side and a bottom surface, the arcuate tray portion sized and configured to at least partially cover a person's upper tooth set, and an elastic lower tooth set-engaging tab portion extending from the front of the arcuate tray portion, which tab portion, in its relaxed state, further extends downward below the bottom surface of the tray portion and partially rearward toward the rear of the tray portion so that, rearward of the point the tab portion extends from the tray portion, a space is present between the bottom surface of the tray portion and the tab below.

9 Claims, 4 Drawing Sheets

MOUTH GUARD FOR THE PREVENTION OF JAW CLENCHING AND TEETH GRINDING

CROSS-REFERENCE TO RELATED APPLICATIONS

This application claims the benefit of U.S. provisional patent application Ser. No. 61/966,381 filed Feb. 24, 2014, which is hereby incorporated by reference in its entirety.

FIELD OF THE INVENTION

The invention relates to the field of bruxism-preventing devices.

BACKGROUND OF THE INVENTION

Bruxism is the excessive grinding of the teeth and/or excessive clenching of the jaw. It is an oral parafunctional activity; i.e., it is unrelated to normal function such as eating or talking. Bruxism is a common problem with reports of it prevalence in the range of 8-31% in the general population. Bruxism may occur with a range of severity from mild to severe. Symptoms commonly associated with bruxism include hypersensitive teeth, aching jaw muscles, and headaches. Bruxism may also cause tooth wear and even damage or break teeth and dental restorations such as crowns and fillings. Bruxism may occur during sleep (sleep bruxism) or during wakefulness (awake bruxism). Teeth grinding and jaw clenching may also lead to and/or exacerbate temporomandibular joint dysfunction (TMD, TMJD).

U.S. Publication No. 2004/0038172 discloses preformed thermo-formable trays made from polymer including ultra-low density polyethylene and which include a removable front handle for handling the tray during heating in hot water.

U.S. Publication No. 2013/0130193 discloses oral orthosis handles for handling thermo-formable oral orthoses during heating in hot water.

What is needed and provided by the present invention are new and improved devices for preventing and ameliorating the jaw clenching and grinding of teeth associated with bruxism.

SUMMARY OF THE INVENTION

One embodiment of the invention provides a mouth guard for the prevention of bruxism that includes:

an arcuate tray portion having a front portion, a rear, a bottom surface, a radially inner side wall and a radially outer side wall, the arcuate tray portion sized and configured to at least partially cover a person's upper or lower tooth set with the front teeth covered by the front portion; and an elastic tab portion extending from the front of the tray portion and continuing to extend beneath and spaced apart from the bottom surface of the tray portion in an at least substantially horizontal direction so that when the tray portion covers a person's top or bottom teeth the tab portion is disposed between the person's top teeth and bottom teeth. The tab acts as a spring to resist full closure of the jaws, so that the posterior teeth cannot touch each other.

A related embodiment of the invention provides a mouth guard for the prevention of bruxism that includes:

an arcuate tray portion having a front, a rear and two sides, the arcuate tray portion sized and configured to at least partially cover a person's upper or lower tooth set and including an arcuate bottom wall having an inner edge, an outer edge, a top surface and a bottom surface defining the bottom surface of the tray portion, an inner side wall extending upward from the inner edge of the bottom wall and an outer side wall extending upward from the outer edge of the bottom wall, said walls collectively defining an arcuate channel; and an elastic tab portion extending from the inner or outer side wall at the front of the tray portion, continuing to extend beneath and spaced apart from the bottom surface of the tray portion toward and beyond the side wall opposite the side wall from which it extends. When the mouth guard is worn, the elastic tab is disposed between the user's upper and lower teeth and acts as a spring resisting the closure of the jaws.

A further embodiment of the invention provides a mouth guard for the prevention of bruxism that includes:

an arcuate tray portion having a front portion, a rear, a bottom surface, a radially inner side wall and a radially outer side wall, the arcuate tray portion sized and configured to at least partially cover a person's upper or lower tooth set with the front teeth covered by the front portion; and an elastic tab portion extending from the front of the tray portion and continuing to extend beneath and spaced apart from the bottom surface of the tray portion in an at least substantially horizontal direction so that when the tray portion covers a person's top or bottom teeth the tab portion is disposed between the person's top teeth and bottom teeth in a configuration resisting closure of the jaws (i.e., the biting together of the teeth).

A still further embodiment of the invention provides a mouth guard for the prevention of bruxism that includes:

an arcuate tray portion having a front portion, a rear, a bottom surface, a radially inner side wall and a radially outer side wall, the arcuate tray portion sized and configured to at least partially cover a person's upper or lower tooth set with the front teeth covered by the front portion; and at least one spring member connected to and extending from the tray portion, such as connected to and extending from the front portion of (the front teeth engaging portion of) the tray portion and disposed at least in part below the bottom surface of the tray portion so that when the tray portion covers a person's top or bottom teeth the spring member is disposed between the person's top teeth and bottom teeth in a configuration resisting closure of the jaws (i.e., the biting together of the teeth).

The invention also provides methods of using the mouth guards.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1A:
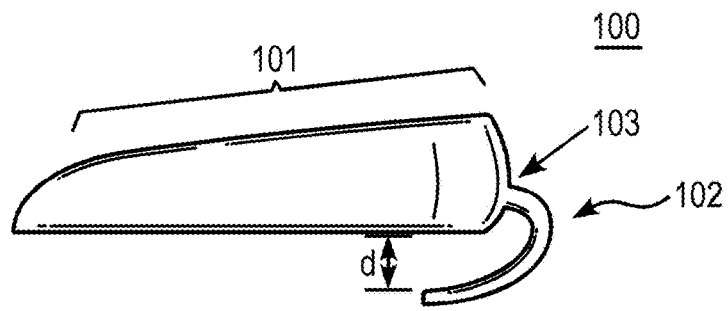
FIG. 1A shows a side view of a mouth guard embodiment of the invention.

The invention provides mouth guards that include an arcuate tray sized and configured to fit over a user's top tooth set and at least one elastic member connected to the tray that is disposed at least in part beneath the tray and in such a configuration than when the mouth guard is worn, the elastic member is disposed between the user's upper and lower teeth in a configuration resisting, i.e., providing force against, the biting together of the top and bottom teeth.

In one embodiment, the invention provides a mouth guard that includes an arcuate tray portion having a front, a rear, top surface and bottom surface, the arcuate tray portion sized and configured to at least partially cover a person's upper tooth set, and a flexible elastic lower tooth set-engaging tab extending from the front of the of the arcuate tray portion which, in its relaxed state (i.e., with no external forces applied), further extends downward below the bottom surface of the tray portion and partially rearward toward the rear of the tray portion so that rearward of the point the tab portion extends from the tray portion a space is present between the bottom surface of the tray portion and the tab portion below. The tab portion may extend out from the middle of the arch of tray portion. There may one or more tab portions. For example, there may be one middle-disposed tab portion, or two tab portions (bilaterally symmetrically disposed with respect to the curvature of the tray portion), or three tab portions with a middle tab portion flanked on each side by a further tab portion to give a bilaterally symmetric configuration.

The rearward/inward extension of the tab(s) may, for example be no more than 3.0 cm from the front-most part of the front center of the tray portion, for example, in the range of 1.0 cm to 3.0 cm therefrom, 1.5 cm to 3.0 cm therefrom, or 1.5 cm to 3.0 therefrom. The unfolded length (measuring its length around the curves) of each tab may, for example, be in the range of 2.0 cm to 3.5 cm, for example at or around 2.5 cm. The thickness of each tab may be at least substantially uniform and may be at least substantially uniform across multiple tabs in multiple tab embodiments. The thickness of the tab(s) may, for example, be in the range of 0.1 to 0.4 cm, such as 0.2 cm to 0.3 cm, such as at or about 0.2 cm or 0.3 cm. The vertical distance between the bottom of the tray portion of the mouth guard and the top-facing surface of the tab portion below it may, for example, be in the range of 0.5 cm to 2.0 cm, such as in the range of 0.5 cm to 1.5 cm, but may vary somewhat due to the curvature and angular disposition of the tab as it extends.

The tray portion may, for example, be sized and configured to cover all of a user's upper teeth or to only extend rearward on each side to such an extent that one or two or more of the rearward-most teeth on each side remain uncovered when the tray is worn. The size of the tray portion of a mouth guard according to the invention may also be adjusted by trimming/cutting away rearward most portions on each side of the tray, as desired or needed by particular user. The back (radially inner) wall of the tray portion may, for example, generally have a lower vertical height than the front (radially outer) wall of the tray portion. One or both of the front wall and the rear wall of the tray portion may taper down toward the bottom wall as they approach the rear end of the mouth guard on each of its sides.

The width of the inner channel of the tray portion of the mouth guard into which the user's upper teeth are inserted may, for example, be in the range of 0.8 cm to 1.5 cm. The width may narrow across the front tooth portion, for example, be at or around 0.8 cm and widen in the molar portions, for example, be in the range of 1.2 to 1.5 cm wide. The wall thickness of the sides forming the tray portion may, for example, be in the range of at or about 0.3 cm to 0.4 cm.

The length of the mouth guard measured from a line bisecting the apex of the arch may, for example, be in the range of 4.0 cm to 6.0 cm, such as 4.5 cm to 5.5 cm. The mouth guards of the invention may generally be provided in varying sizes to fit jaws of different sizes.

As used herein with respect to recited numerical values, the term "about" means+/−5% of the recited value.

The mouth guard may, for example, be at least partially made from a polymer, such as but not limited to a natural or synthetic polymer that is both springy (elastic) and flexible. The mouth guard may, for example, be made from a silicone rubber or an ultra low density polyethylene (ULDPE), either alone or blended with one or more additional polymers, e.g., ethylene-vinyl acetate copolymer (EVA), ϵ-polycaprolactone (PCL), other types of polyethylene, polypropylene, or other plastic polymer materials. Plasticizers or flow additives known in the thermoplastic arts may be used as to modify the properties of the thermoplastic material as desired. The mouth guard may, for example, be one-piece or be composed of multiple pieces joined together, for example, by adhesives, by welding and/or by fasteners. The mouth guard may, for example, be produced as one-piece in an injection molding process or by any method of manufacture known in the art. In another method of manufacture, the mouth guard may be injection molded from a polymeric material as the tray portion with a flat (not curved back) tab(s) portion extending from it, and the molded article is then placed in a bending jig, for example, one that is heated at least temporarily, to introduce and set the desired curvatures as recited herein into the tab(s).

It is preferred that at least the one or more tab portions of the mouth guards are elastic, such as formed from an elastic polymer, so that they may act as springs resisting closure of the jaws, for example, in the manner of cantilever springs.

In one embodiment, the tray portion of the mouth guard is placed over the human user's top teeth with the tab extending from the front of the tray portion and turning downward and rearward so that the rearward extending portion of the tab portion can touch and engage the front lower teeth of the user. Since at least the tab portion of the mouth guard can be made from a springy polymer, when the user's jaw's close, the tab resists the closure with a downward and slightly frontward force against the user's lower teeth (and thus on the lower jaw). In this manner, the jaw clenching and teeth grinding associated with bruxism is at least partially prevented.

The invention also provides corresponding embodiments in which the tab extends rearward from the front portion of an upper teeth-wearable tray portion of the mouth guard (for example, from the rear wall, i.e., radially inner wall, of the front teeth-covering part of the tray portion), then downward and then frontward. However, this embodiment is not preferred since it applies a slightly rearward force on the lower teeth (and thus lower jaw). The invention also provides mouth guards to be worn on a user's lower teeth and in this case, to obtain the preferred outward force on the lower jaw, the analogous tab may extend first from the inner wall of the front of the tray portion, move upward (with respect to vertical axis of the user) and forward between the front and bottom teeth of the user. Thus, the preferred configurations of cantilever type tabs for upper and lower teeth worn mouth guards of the invention are opposite, but the invention provides that either configuration may be used for an upper or lower teeth worn mouth guard.

The invention also provides a method of using any of the mouth guard embodiments and variations thereof as described herein for, for example, the prevention of bruxism in a human user in need of such prevention (afflicted by bruxism) and/or for the amelioration/treatment of TMD or symptoms thereof by a human user in need of such amelioration/treatment (afflicted by TMD) that includes the step of disposing the tray portion of the mouth guard over the user's top or bottom teeth so that the tab portion is disposed between the user's top and bottom teeth, such as between their top front and bottom front teeth. The mouth guard may be worn in this manner during sleep and/or during wakefulness and, for example, it may be worn for a period of time, such as at least one hour, at least two hours, at least three hours or for example for a period of time in the range of 30 minutes to 10 hours at a time, understanding that the period of wear may be uninterrupted or a user may intermittently remove and then put the mouth guard back on. The method may further include the step of providing the mouth guard that is to be worn.

The tab member of the mouth guards may be a curved flexible strip extending out from the exterior front and center of the guard and curving back toward the rear so that it will extend back into the user's mouth when the mouth guard is worn on the upper or lower teeth. The tab may have any shape and may be at least substantially triangular or otherwise widen as it extends from the tray portion of the mouth guard. The width of the tab may, for example, be equal to, about or up to 3.0 cm at its widest point. For example, the maximum width of the tab may be in the range of equal to or about 1.0 cm to equal to or about 3.0 cm.

Various aspects of the invention are further described below with respect to the appended drawings.

FIG. 1A shows a side view of a mouth guard embodiment 100 of the invention. Mouth guard 100 includes a tray portion 101 sized and configured to fit over a person's upper (or lower) set of teeth and a tab portion 102 that extends out from the front tray portion 101 from connection point 103. As shown, tab 102 extends forward and downward, turning back inward (rearward) with a distance d between the bottom of tray portion 101 and the surface of tab 102 beneath it.

Figure 1B:
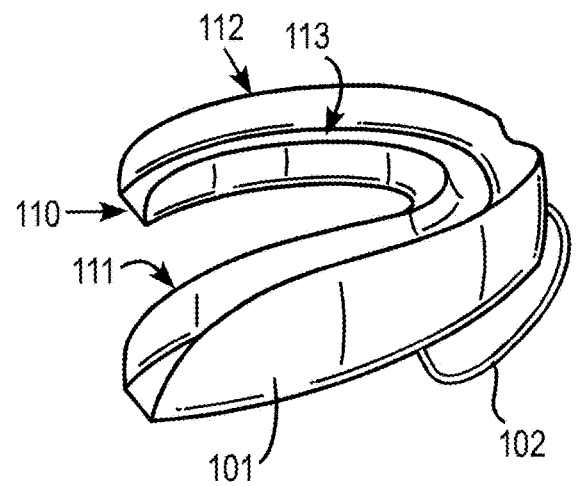
FIG. 1B shows a top perspective view of the embodiment shown in FIG. 1B

FIG. 1B shows a top perspective view of the embodiment shown in FIG. 1B. Tray portion 101 includes a bottom wall 110, a rear (inner) side wall 111, and a front (outer) side wall 112 that together form a channel 113 in which the user's upper (or lower) teeth are disposed when the apparatus is worn. Tab 102 is shown extending from the front of tray portion 101 and curving around beneath the front portion of tray portion 101.

Figure 1C:
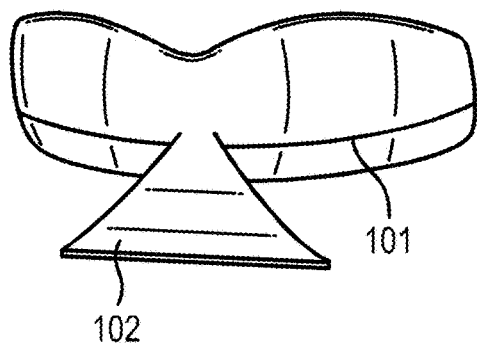
FIG. 1C shows a front view of the embodiment shown in FIGS. 1A and 1B.

FIG. 1C shows a front view of the embodiment shown in the FIGS. 1A and 1B. In the embodiment shown, tab portion 102 has a substantially triangular shape, widening as it extends out from tray 101.

Figure 2:
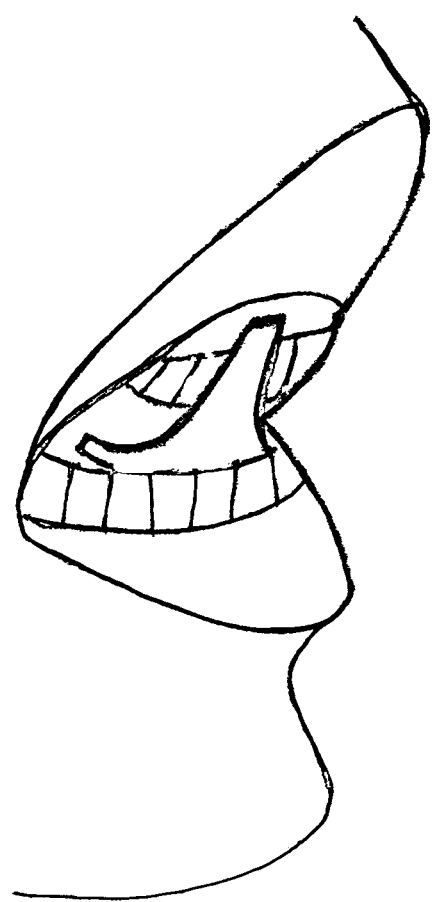
FIG. 2 shows a single tab mouth guard embodiment of the invention like that shown in FIGS. 1A-C worn by a user.

FIG. 2 shows a single elastic tab mouth guard embodiment of the invention like that shown in FIGS. 1A-C worn by a user on their upper teeth.

Figure 3A:
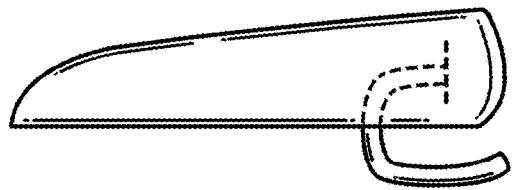
FIG. 3A shows a side view of a mouth guard embodiment of the invention in which an elastic tab member extends from the rear wall of the tray portion of the mouth guard, curves below the bottom surface of the tray portion and extends forward past the front wall of the tray portion.

FIG. 3A shows a side view of a mouth guard embodiment of the invention in which an elastic tab member extends from the rear wall of the tray portion of the mouth guard, curves below the bottom surface of the tray portion and extends forward past the front wall of the tray portion.

Figure 3B:
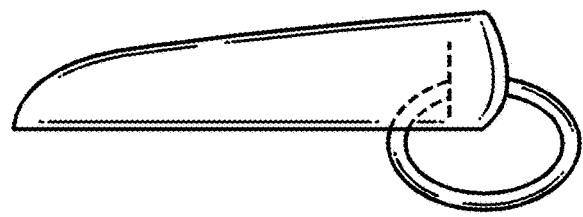
FIG. 3B shows a side view of a mouth guard embodiment of the invention in which the elastic tab member is connected to the tray portion of the mouth guard at each end, to the front wall of the tray portion on one end and to the back wall of the tray portion of the mouth guard at the other end.
Figure 3C:
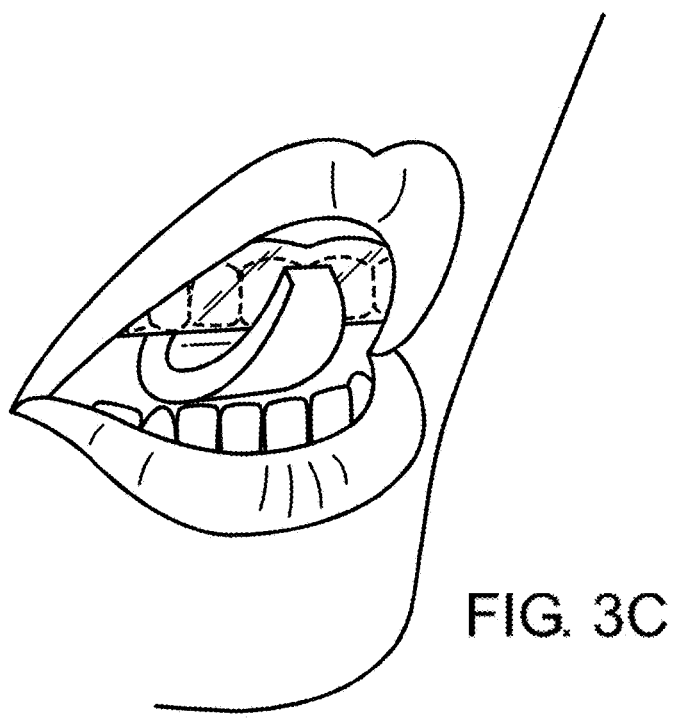
FIG. 3C is an illustration showing a mouth guard embodiment like that shown in FIG. 3B, as worn by a user on their top teeth.

FIG. 3B shows a side view of a mouth guard embodiment of the invention in which the elastic tab member is connected to the tray portion of the mouth guard at each end, namely, to the front wall of the tray portion on one end and to the back wall of the tray portion of the mouth guard at the other end. The tab acts as an elliptical spring to resist closure of the jaws when the mouth guard is worn. FIG. 3C is an illustration showing a mouth guard embodiment like that shown in FIG. 3C, as worn by a user on their top teeth.

Figure 4:
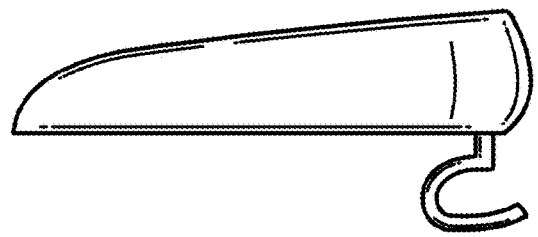
FIG. 4 shows a side view of a mouth guard embodiment of the invention in which an elastic tab portion extends from the bottom surface of the front of the tray portion of the mouth guard in the form of a top-tethered C-shape.

FIG. 4 shows a side view of a mouth guard embodiment of the invention in which an elastic tab portion extends from the bottom surface of the front of the tray portion of the mouth guard in the form of a tethered C-shape. The invention also provides corresponding embodiments in which the C-shaped member opens in the opposite direction. Similar embodiments having an elliptical or circular closed elastic member/configuration, rather than a laterally open C-configuration, are also provided by the invention.

Figure 5A:
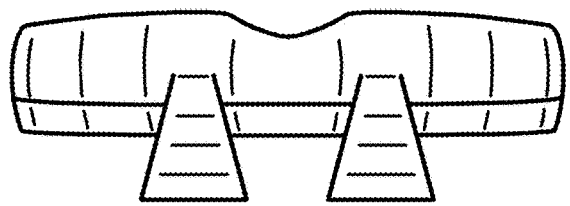
FIG. 5A shows a front view of a mouth guard embodiment of the invention having two elastic tabs extending from the front of the tray portion of the mouth guard and further extending below the bottom surface of the tray portion and toward the rear of the mouth guard past the rear wall of the front of the tray portion of the mouth guard.

FIG. 5A shows a front view of a mouth guard embodiment of the invention having two elastic tabs extending from the front of the tray portion of the mouth guard and further extending below the bottom surface of the tray portion and rearward past the rear wall of the front of the tray portion of the mouth guard.

Figure 5B:
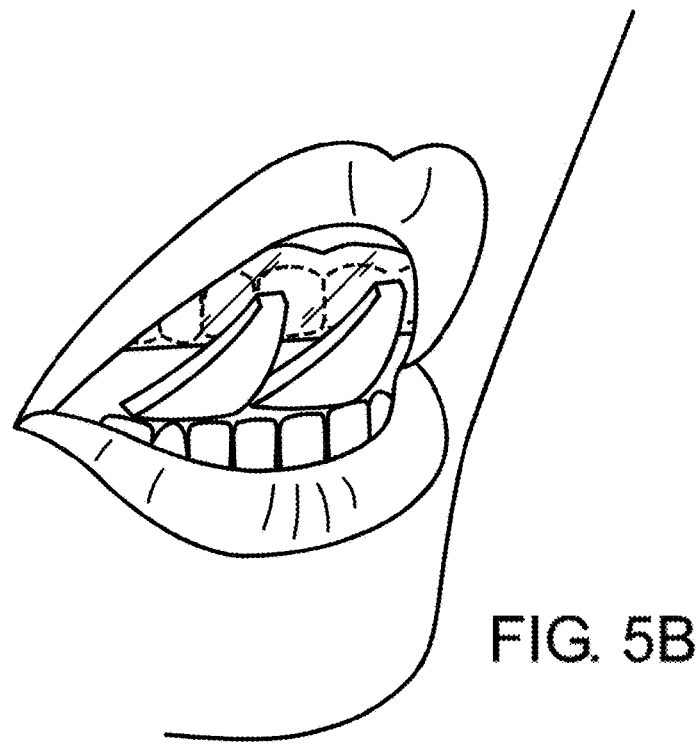
FIG. 5B is an illustration showing a mouth guard embodiment having two elastic tabs like that shown in FIG. 5A worn by a user.

FIG. 5B is an illustration showing a mouth guard embodiment having two elastic tabs like that shown in FIG. 5A, as worn by a user on their top teeth.

Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A mouth guard for the prevention of bruxism, comprising:
    an arcuate tray portion having a front, a rear and two sides, the arcuate tray portion sized and configured to at least partially cover a person's upper or lower tooth set and comprising an arcuate bottom wall having an inner edge, an outer edge, a top surface and a bottom surface defining the bottom surface of the tray portion, an inner side wall extending upward from the inner edge of the bottom wall and an outer side wall extending upward from the outer edge of the bottom wall, said walls collectively defining an arcuate channel; and an elastic tab portion having two ends, the elastic tab portion extending at one of the two ends from the inner side wall at the front of the tray portion, continuing to extend beneath and spaced apart from the bottom surface of the tray portion toward and beyond the side wall opposite the side wall from which it extends so as to be free at the other of the two ends.

2. The mouth guard of claim 1, wherein the elastic tab portion has a width that increases as the tab extends from the inner wall at the front of the tray portion.

3. A method for preventing teeth grinding or jaw clenching, comprising the steps of:

providing a mouth guard according to claim 1;

in a human subject in need of prevention of teeth grinding or jaw clenching, disposing the mouth guard over the subject's top or bottom teeth so that the teeth are disposed in the channel and the elastic tab portion extends between the subject's top teeth and bottom teeth.

4. The method of claim 3, wherein the mouth guard remains over the subject's top or bottom teeth so that the teeth are disposed in the channel and the elastic tab portion extends between the subject's top teeth and bottom teeth while the subject is sleeping.

5. A mouth guard for the prevention of bruxism, comprising:

an arcuate tray portion having a front portion, a rear, a bottom surface, a radially inner side wall and a radially outer side wall, the arcuate tray portion sized and configured to at least partially cover a person's upper or lower tooth set with the front teeth covered by the front portion; and an elastic tab portion extending from the front of the tray portion and continuing to extend beneath and spaced apart from the bottom surface of the tray portion in an at least substantially horizontal direction so that when the tray portion covers a person's top or bottom teeth the elastic tab portion is disposed between the person's top teeth and bottom teeth, wherein the elastic tab portion has a first end attached to the radially outer wall of the tray portion at the front of the mouth guard and an opposite second end attached to the radially inner wall of the tray portion at the front of the mouth guard.

6. A method for preventing teeth grinding or jaw clenching, comprising the steps of:

providing a mouth guard according to claim 5;

in a human subject in need of prevention of teeth grinding or jaw clenching, disposing the mouth guard over the subject's top teeth so that the top teeth are disposed in the tray portion and the elastic tab portion is disposed between the subject's top teeth and bottom teeth.

7. The method of claim 6, wherein the human subject has one or both of bruxism and temporomandibular joint dysfunction (TMD).

8. The method of claim 6, wherein the mouth guard remains over the subject's top teeth so that the top teeth are disposed in the channel and the elastic tab portion extends between the subject's top teeth and bottom teeth while the subject is sleeping.

9. The method of claim 8, wherein the human subject has sleep bruxism.

\* \* \* \* \*